United States Patent [19]
Kanellakopulos et al.

[11] Patent Number: 6,063,798
[45] Date of Patent: May 16, 2000

[54] SUBSTITUTED N-METHYLENETHIOUREAS AS PESTICIDES

[75] Inventors: Johannes Kanellakopulos, Dormagen; Kurt Findeisen; Karl-Heinz Linker, both of Leverkusen; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[21] Appl. No.: 08/981,001

[22] PCT Filed: Jun. 17, 1996

[86] PCT No.: PCT/EP96/02602

§ 371 Date: Dec. 22, 1997

§ 102(e) Date: Dec. 22, 1997

[87] PCT Pub. No.: WO97/01537

PCT Pub. Date: Jan. 16, 1997

[30] Foreign Application Priority Data

Jun. 29, 1995 [DE] Germany ............... 195 23 658

[51] Int. Cl.[7] ................................ A01N 43/40
[52] U.S. Cl. ............ 514/357; 514/341; 514/342; 514/357; 546/270.7; 546/274.7; 546/331
[58] Field of Search ................ 514/341, 342, 514/357, 252, 255, 374, 400, 438, 471; 546/270.7, 274.7, 331; 544/224, 336; 548/204, 235; 549/76, 495

[56] References Cited

U.S. PATENT DOCUMENTS 5,063,236  11/1991  Gsell ........................... 514/318

FOREIGN PATENT DOCUMENTS 0 268 915  1/1988  European Pat. Off. .
0 639 569  2/1995  European Pat. Off. .

*Primary Examiner*—Peter O'Sullivan
*Attorney, Agent, or Firm*—Joseph C. Gil; Lyndanne M. Whalen

[57] ABSTRACT

The present invention relates to new substituted N-methylenethioureas of the general formula (I)

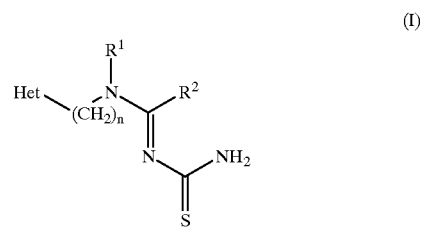

in which n, Het, $R^1$ and $R^2$ have the meanings given in the description, to a process for their preparation, and to their use in pesticides, in particular as insecticides.

10 Claims, No Drawings

SUBSTITUTED N-METHYLENETHIOUREAS AS PESTICIDES

This application is a 371 of PCT/EP96/02602 filed Jun. 17, 1996.

The present invention relates to new substituted N-methylenethioureas, to a process for their preparation, and to their use in pesticides, in particular as insecticides.

The prior art describes N-substituted amidino(thio)ureas and their use as pharmaceuticals, which differ from the N-methylenethioureas of the present application by the presence of a (thio)carbonyl group in the molecule (BE 894 172; U.S. Pat. No. 4,701,457).

Moreover, JP 53 108 970 describes guanidine derivatives which can also be employed in pharmacology for regulating the secretion of gastric acids. An insecticidal action of the compounds is not known from the most relevant prior art.

There have now been found the new substituted N-methylenethioureas of the general formula (I)

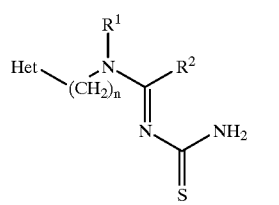

(I)

in which n represents 0, 1 or 2,

Het represents a five- or six-membered heterocyclic group containing 1, 2, 3 or 4 nitrogen atoms and/or one or two oxygen or sulphur atoms as hetero atom ring members—the number of ring hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogeno-alkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, $R^1$ represents hydrogen or alkyl, $R^2$ represents hydrogen, alkyl or one of the groups $NR^3R^4$, $SR^5$ or $OR^5$, $R^3$ represents hydrogen or alkyl, $R^4$ represents hydrogen or alkyl, $R^5$ represents alkyl, or $R^1$ and $R^3$ or $R^1$ and $R^5$ together can form an optionally substituted ethylene or propylene bridge which can optionally be interrupted by 1 further hetero atom.

Furthermore, it has been found that the new substituted N-methylenethioureas of the general formula (I) are obtained when the corresponding N'-aralkyl-N-cyano-amidine of the general formula (II)

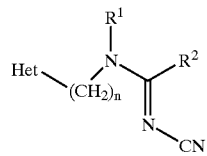

(II)

in which

Het, n, $R^1$ and $R^2$ have the abovementioned meaning are reacted with Lawessons's reagent, if appropriate in the presence of a diluent and if appropriate with the exclusion of moisture.

Surprisingly, the new substituted N-methylenethioureas of the general formula (I) are distinguished in a surprising manner by a potent insecticidal activity.

The invention preferably relates to compounds of the formula (I) in which n represents a number 0, 1 or 2, Het represents a five- or six-membered heterocyclic group from the series consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which is optionally substituted by fluorine, chlorine, bromine, iodine, cyano, nitro, $C_1$–$C_4$-alkyl (which is optionally substituted by fluorine and/or chlorine), $C_2$–$C_4$-alkenyl (which is optionally substituted by fluorine and/or chlorine), $C_2$–$C_4$-alkinyl, $C_1$–$C_4$-alkoxy (which is optionally substituted by fluorine and/or chlorine), $C_3$–$C_4$-alkenyloxy (which is optionally substituted by fluorine and/or chlorine), $C_3$–$C_4$-alkinyloxy, $C_1$–$C_4$-alkylthio (which is optionally substituted by fluorine and/or chlorine), $C_3$–$C_4$-alkenylthio (which is optionally substituted by fluorine and/or chlorine), $C_3$–$C_4$-alkinylthio, $C_1$–$C_4$-alkylsulphinyl (which is optionally substituted by fluorine and/or chlorine), $C_1$–$C_4$-alkylsulphonyl (which is optionally substituted by fluorine and/or chlorine), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl, and $R^1$ represents hydrogen or $C_1$–$C_6$-alkyl, $R^2$ represents hydrogen, $C_1$–$C_6$-alkyl or one of the groups $NR^3R^4$, $SR^5$ or $OR^5$, $R^3$ represents hydrogen or $C_1$–$C_6$-alkyl, $R^4$ represents hydrogen or $C_1$–$C_6$-alkyl, $R^5$ represents $C_1$–$C_6$-alkyl, or $R^1$ and $R^3$ or $R^1$ and $R^5$ together form an optionally substituted ethylene or propylene bridge which can optionally be interrupted by 1 further oxygen, nitrogen or sulphur atom and optionally substituted by the following substituents:

fluorine, chlorine, bromine, cyano, $C_1$–$C_4$-alkyl, $C_1$–$C_4$-alkoxy, $C_2$–$C_4$-alkenyl, $C_2$–$C_4$-alkinyl.

The invention particularly relates to compounds of the formula (I) in which n represents a number 0, 1 or 2, Het represents a five- or six-membered heterocyclic group from the series consisting of pyrazolyl, 1,2,4-triazolyl, oxazolyl, isoxazolyl, thiazolyl, isothiazolyl, 1,2,5- thiadiazolyl, pyridyl, pyrazinyl and pyrimidinyl, which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine) or $C_1$–$C_2$-alkylsulphonyl (which is optionally substituted by fluorine and/or chlorine), $R^1$ represents hydrogen or $C_1$–$C_4$-alkyl, $R^2$ represents hydrogen, $C_1$–$C_4$-alkyl or one of the groups $NR^3R^4$, $SR^5$ or $OR^5$, $R^3$ and $R^4$ in each case represent hydrogen or $C_1$–$C_4$-alkyl, $R^5$ represents $C_1$–$C_4$-alkyl, or $R^1$ and $R^3$ or $R^1$ and $R^5$ together can form an optionally substituted ethylene or propylene bridge which can optionally be interrupted by 1 further oxygen, nitrogen or sulphur atom and optionally substituted by the following substituents:

fluorine, chlorine, bromine, cyano, methyl, ethyl, n-, i-propyl and n-, i-, s-, t-butyl.

Very particularly preferred compounds of the formula (I), are those in which n represents the number 1, Het represents pyridyl which is optionally substituted by fluorine or chlorine or thiazolyl which is substituted by bromine or chlorine, $R^1$ represents hydrogen, methyl or ethyl, $R^2$ represents hydrogen, methyl or ethyl or one of the groups $NR^3R^4$, $SR^5$ or $OR^5$, $R^3$ and $R^4$ in each case represent hydrogen, methyl or ethyl, $R^5$ represents methyl or ethyl, or $R^1$ and $R^3$ or $R^1$ and $R^5$ together form a —$CH_2$–$CH_2$— group.

If, for example, N-(2-chloro-5-pyridylmethyl) according to the invention is used as starting material, the reaction in question can be represented by the following equation:

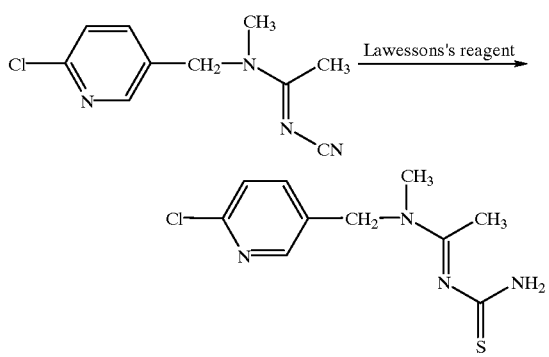

Formula (II) provides a general definition of the N-cyano compounds to be used as starting materials in the process according to the invention. In this formula (II), Het, n, $R^1$ and $R^2$ preferably have the meaning which have already been mentioned in connection with the description of the substances of the formula (I) according to the invention as being preferred for Het, n, $R^1$ and $R^2$.

The compounds of the formula (II) are known and/or can be prepared by known methods.

The process according to the invention for the preparation of the new compounds of the formula (I) is preferably carried out using diluents. Suitable diluents are all inert organic solvents which are customary for the reaction.

Examples of such diluents embrace ethers, such as diethyl ether, di-isopropyl ether, methyl-tert-butyl ether, dimethoxy ethane, dioxane, tetrahydrofuran, acid amides, such as dimethylformamide, dimethylacetamide, N-methylpyrrolidone, and sulphoxides, such as dimethyl sulphoxide.

The process according to the invention for the preparation of the new compounds of the formula (I) is preferably carried out using Lawessons's reagent [2,4-bis-(4-methoxyphenyl)-1,3-dithia-2,4-diphosphetane 2,4-disulphide; Bull. Soc. Chim. Belg. 87,223,229,299,525 (1978)].

The reaction temperatures for the process according to the invention can be varied within a substantial range. In general, the process is carried out at temperatures between 0° C. and 50° C., preferably at temperatures between 15° C. and 30° C.

The process according to the invention is generally carried out under atmospheric pressure. However, it is also possible to carry out the process under elevated or reduced pressure.

To carry out the process for the preparation of the new compounds of the formula (I), the starting materials required in each case are generally employed in approximately equimolar amounts. However, it is also possible to use one of the components employed in each case in a larger excess. The reactions are generallly carried out in a suitable diluent, and the reaction mixture is stirred for several hours at the temperature required in each case. Working-up in the process according to the invention is carried out in each case by customary methods.

The preparation of the compounds according to the invention can be seen from the examples which follow.

Preparation Example

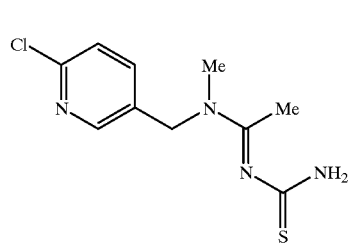

(1)

A mixture of 3.0 g (13.4 mmol) of "N1-25" and 5.25 g of Lawesson's reagent in 50 ml THF is stirred for 12 hours at 50° C. with the exclusion of moisture. The solvent is distilled off under reduced pressure, the residue is treated with 25 ml of 1M sodium carbonate solution, and the mixture is extracted using ethyl acetate. Chromatography (silica gel, ethyl acetate/cyclohexane 1:1) of the residue obtained after separation, drying and distillation of the organic phase yields 1.1 g (31%) of product 1-thiacarbamoyl-3-N-methyl-3-N-(6-chloopyridyl-3-yl) methylacetamidine of log P=1.58 (acidic).

Other compounds of the formula (I) as listed in the table below can be prepared analogously to the preparation example:

TABLE 1

| n | Het | R¹ | R² | Physical data |
|---|---|---|---|---|
| 2 | 1 | Cl-pyridyl | | —CH₂—CH₂—S— | m.p. = 150° C. |
| 3 | 1 | Cl-pyridyl | | —CH₂—CH₂—NH— | log P = 0.81 (acidic) |

The active compounds are suitable for combating animal pests, preferably arthropods, particularly insects encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Ancanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

The active compounds of the formula (I) according to the invention are distinguished by an outstanding insecticidal activity. They show an outstanding action against beetle larvae, such as, for example, *Phaedon cochleariae* and *Diabrotica balteata,* aphids, such as, for example, *Myzus persicae* and leafhoppers, such as, for example, *Nephotettix cincticeps* in particular when employed as foliar- and soil-acting insecticides.

In addition, the active compounds of the formula (I) according to the invention also have an outstanding root-systemic action.

The new compounds are therefore particularly suitable for use in combating leaf- and soil-dwelling insects and as root-systemic active compounds.

Furthermore, some of the new compounds also have a fungicidal action against *Pyricularia oryzae* and *Pellicularia sasakii.*

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surfactants, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl iso-butyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgute, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compound, preferably between 0.5 and 90%.

The active compounds can be present in their commercially available formulations and in the use forms, prepared from these formulations, as a mixture with other active compounds, such as insecticides, attractants, sterilants, acaricides, nematicides, fungicides, growth-regulating substances or herbicides. The insecticides include amongst others, for example, phosphates, carbamates, carboxylates, chlorinated hydrocarbons, phenylureas, substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be actively effective itself.

The active compound content of the use forms prepared from the commercially available formulations can vary within a wide range. The active compound concentration of the use forms may be from 0.0000001 to 95% by weight of active compound, preferably between 0.0001 and 1% by weight.

The compounds are employed in a customary manner appropriate for the use forms.

When used against hygiene and stored-product pests, the active compounds are distinguished by an outstanding residual action on wood and clay and by a good stability to alkali and limed substrates.

The biological activity of the compounds according to the invention will be illustrated with the aid of the following examples.

EXAMPLE

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the specified periods of time, the destruction in % is determined. 100% means that all the beetle larvae have been killed; 0% means that none of the beetle larvae have been killed.

In this test, a superior activity compared with the prior art is shown, for example, by the following compounds of the preparation examples:

TABLE 1

(plant-injurious insects)
Phaedon larvae test

| Active compounds | Active compound concentration in % | Degree of destruction in % after 7 days |
|---|---|---|
| (2) | 0.1 | 100 |

TABLE 1-continued (plant-injurious insects)
Phaedon larvae test

| Active compounds | Active compound concentration in % | Degree of destruction in % after 7 days |
|---|---|---|
| (compound 1: 6-chloropyridin-3-yl-CH₂-N(CH₃)-C(CH₃)=N-C(=S)NH₂) | 0.1 | 100 |
| (compound 3: 6-chloropyridin-3-yl-CH₂-N-imidazolidine with =N-C(=S)NH₂ substituent) | 0.1 | 100 |

EXAMPLE

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (Plutella maculipennis) while the leaves are still moist.

After the specified periods of time, the destruction in % is determined. 100% means that all the caterpillars have been killed; 0% means that none of the caterpillars have been killed.

In this test, a superior activity compared with the prior art is shown, for example, by the following compounds of the preparation examples:

TABLE 2

(plant-injurious insects)
Plutella test

| Active compounds | Active compound concentration in % | Degree of destruction in % after 7 days |
|---|---|---|
| (compound 2: 6-chloropyridin-3-yl-CH₂-N-thiazolidine with =N-S substituent and S=C-NH₂) | 0.1 | 100 |

EXAMPLE

Spodoptera Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the fall army worm *Spodoptera frugiperda*) while the leaves are still moist.

After the specified periods of time, the destruction in % is determined. 100% means that all the caterpillars have been killed; 0% means that none of the caterpillars have been killed.

In this test, a superior activity compared with the prior art is shown, for example, by the following compounds of the preparation examples:

TABLE 3

(plant-injurious insects)
Spodoptera test

| Active compounds | Active compound concentration in % | Degree of destruction in % after 7 days |
|---|---|---|
| (compound 2) | 0.1 | 100 |

EXAMPLE

Nephotettix Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are infested with the green rice leafhopper (*Nephotettix cincticeps*) while the seedlings are still moist.

After the specified periods of time, the destruction in % is determined. 100% means that all the leafhoppers have been killed; 0% means that none of the leafhoppers have been killed.

In this test a superior activity compared with the prior art is shown, for example, by the following compounds of the preparation examples:

TABLE 4

(plant-injurious insects)
Nephotettix test

| Active compounds | Active compound concentration in % | Degree of destruction in % after 6 days |
|---|---|---|
| 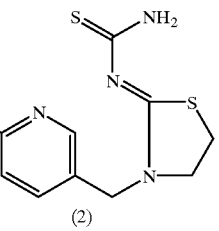 (2) | 0.1 | 100 |
| 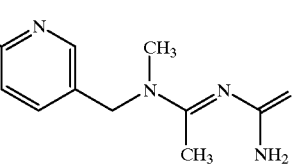 (1) | 0.1 | 90 |
| 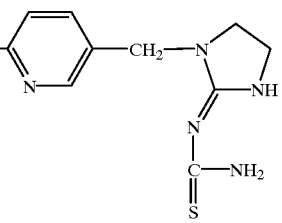 (3) | 0.1 | 100 |

EXAMPLE

Myzus Test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*), which are severely infected with the peach aphid (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, superior activity compared with the prior art is shown, for example, by the following compounds of the preparation examples:

TABLE 5

(plant-injurious insects)
Myzus test

| Active compounds | Active compound concentration in % | Degree of destruction in % after 7 days |
|---|---|---|
| 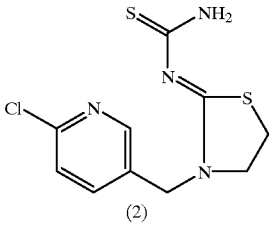 (2) | 0.1 | 98 |
| 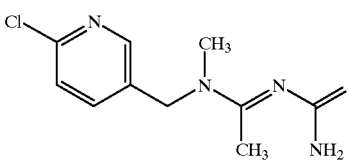 (1) | 0.1 | 80 |
| 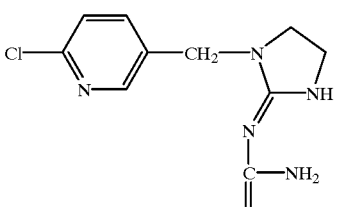 (3) | 0.1 | 100 |

EXAMPLE

Blowfly Larvae Test/Development-Inhibitory Action
Test animals: Lucila cuprina larvae
Solvent: 35 parts by weight of ethylene glycol monomethyl ether
35 parts by weight of nonylphenol polyglycol ether To produce a suitable formulation. 3 parts by weight of the active compound are mixed with 7 parts of the abovementioned solvent/emulsifier mixture and the emulsion concentrate thus obtained is diluted with water to the desired concentration.

About 20 Lucilia cuprina larvae are introduced into a test tube which contains approx. 1 cm$^3$ of horse meat and 0.5 ml of the preparation of active compound to be tested. After 24 and 48 hours, the activity of the preparation of active compound is determined. The test tubes are transferred into beakers whose bottoms are covered with sand. After a further two days, the test tubes are removed and the pupae counted.

The action of the preparation of active compound is assessed on the basis of the number of the hatched flies after 1.5 times the development time and the untreated control. 100% means that none of the flies have hatched; 0% means that all the flies have hatched normally.

In this test, a superior action compared with the prior art is shown, for example, by the following compounds of the preparation examples:

TABLE 6

Blowfly larvae test

| | Concentration | % Action/destruction |
|---|---|---|
| according to the invention | | *Lucillia cuprina* |
| (2) | 1000 | 100 |
| (3) | 1000 | 100 |

EXAMPLE

Cockroach Test

Test animals: Periplaneta americana

Solvent: 35 parts by weight of ethylene glycol monomethyl ether

Emulsifier: 35 parts by weight of nonylphenyl polyglycol ether

To produce a suitable formulation, three parts by weight of the active compound are mixed with seven parts of the abovementioned solvent/emulsifier mixture and the emulsion concentrate thus obtained is diluted with water to the desired concentration.

2 ml of this preparation of active compound are pipetted on to paper filter discs (Ø 9.5 cm) in Petri dishes of a suitable size. After the filter discs have dried, 5 test animals *P. americana* are introduced and covered.

After 3 days, the activity of the preparation of active compound is determined. 100% means that all the cockroaches have been killed; 0% means that none of the cockroaches have been killed.

In this test, a superior action compared with the prior art is shown, for example, by the following compounds of the preparation example.

TABLE 7

Cockroach test

| | Concentration | % Action/destruction |
|---|---|---|
| according to the invention | | *Periplaneta americana* |
| (3) | 1000 | 100 |

What is claimed is:

1. A substituted N-methylenethiourea of the general formula (I)

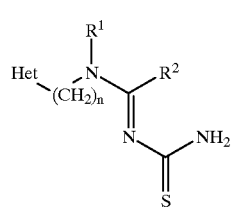

(I)

wherein n represents 0, 1 or 2,

Het represents a five-membered heterocyclic group containing 1 nitrogen atom optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, $R^1$ represents hydrogen or alkyl, $R^2$ represents hydrogen, alkyl or one of the groups $NR^3R^4$, $SR^5$ or $OR^5$, $R^3$ represents hydrogen or alkyl, $R^4$ represents hydrogen or alkyl, $R^5$ represents alkyl, or $R^1$ and $R^3$ or $R^1$ and $R^5$ together can form an optionally substituted ethylene or propylene bridge.

2. A substituted N-methylenethiourea of the general formula (I) according to claim 1, wherein n represents a number 0, 1 or 2, Het represents pyridyl, which is optionally substituted by fluorine, chlorine, bromine, iodine, cyano, nitro, $C_1$–$C_4$-alkyl (which is optionally substituted by fluorine and/or chlorine), $C_2$–$C_4$-alkenyl (which is optionally substituted by fluorine and/or chlorine), $C_2$–$C_4$-alkinyl, $C_1$–$C_4$-alkoxy (which is optionally substituted by fluorine and/or chlorine), $C_3$–$C_4$-alkenyloxy (which is optionally substituted by fluorine and/or chlorine), $C_3$–$C_4$-alkinyloxy, $C_1$–$C_4$-alkylthio (which is optionally substituted by fluorine and/or chlorine), $C_3$–$C_4$-alkenylthio (which is optionally substituted by fluorine and/or chlorine), $C_3$–$C_4$-alkinylthio, $C_1$–$C_4$-alkylsulphinyl (which is optionally substituted by fluorine and/or chlorine), $C_1$–$C_4$-alkylsulphonyl (which is optionally substituted by fluorine and/or chlorine), amino, $C_1$–$C_4$-alkylamino, di-($C_1$–$C_4$-alkyl)amino, phenyl, phenoxy, phenylthio, phenylamino, benzyl, formylamino, $C_1$–$C_4$-alkyl, carbonylamino, formyl, carbamoyl, $C_1$–$C_4$-alkyl-carbonyl and/or $C_1$–$C_4$-alkoxy-carbonyl, and $R^1$ represents hydrogen or $C_1$–$C_6$-alkyl, $R^2$ represents hydrogen, $C_1$–$C_6$-alkyl or one of the groups $NR^3R^4$, $SR^5$ or $OR^5$, $R^3$ represents hydrogen or $C_1$–$C_6$-alkyl, $R^4$ represents hydrogen or $C_1$–$C_6$-alkyl, $R^5$ represents $C_1$–$C_6$-alkyl, or $R^1$ and $R^3$ or $R^1$ and $R^5$ together form an optionally substituted ethylene or propylene bridge which can optionally be optionally substituted by the following substituents:

fluorine, chlorine, bromine, cyano, $C_1$–$C_4$-alkyl, $C_1$–$C_4$-alkoxy, $C_2$–$C_4$-alkenyl, $C_2$–$C_4$-alkinyl.

3. A substituted N-methylenethiourea of the general formula (I) according to claim 1 wherein n represents a number 0, 1 or 2, Het represents pyridyl, which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine) or $C_1$–$C_2$-alkylsulphonyl (which is optionally substituted by fluorine and/or chlorine), $R^1$ represents hydrogen or $C_1$–$C_4$-alkyl, $R^2$ represents hydrogen, $C_1$–$C_4$-alkyl or one of the groups $NR^3R^4$, $SR^5$ or $OR^5$, $R^3$ and $R^4$ in each case represent hydrogen or $C_1$–$C_4$-alkyl, $R^5$ represents $C_1$–$C_4$-alkyl, or $R^1$ and $R^3$ or $R^1$ and $R^5$ together can form an ethylene or propylene bridge which can optionally be substituted by the following substituents:

fluorine, chlorine, bromine, cyano, methyl, ethyl, n-, i-propyl and n-, i-, s-, t-butyl.

4. A substituted N-methylenethiourea of the general formula (I) according to claim 1 wherein n represents the number 1, Het represents pyridyl which is optionally substituted by fluorine or chlorine, $R^1$ represents hydrogen, methyl or ethyl, $R^2$ represents hydrogen, methyl or ethyl or one of the groups $NR^3R^4$, $SR^5$ or $OR^5$, $R^3$ and $R^4$ in each case represent hydrogen, methyl or ethyl, $R^5$ represents methyl or ethyl, or $R^1$ and $R^3$ or $R^1$ and $R^5$ together form a —$CH_2$—$CH_2$— group.

5. A process for the preparation of a substituted N-methylenethiourea of the general formula (I)

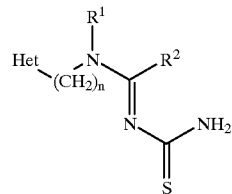

(I)

wherein n represents 0, 1 or 2,

Het represents a five- or six-membered heterocyclic group containing 1, 2, 3 or 4 nitrogen atoms and/or one or two oxygen or sulphur atoms as hetero atom ring members—the number of ring hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, $R^1$ represents hydrogen or alkyl, $R^2$ represents hydrogen, alkyl or one of the groups $NR^3R^4$, $SR^5$ or $OR^5$, $R^3$ represents hydrogen or alkyl, $R^4$ represents hydrogen or alkyl, $R^5$ represents alkyl, or $R^1$ and $R^3$ or $R^1$ and $R^5$ together can form an optionally substituted ethylene or propylene bridge which can optionally be interrupted by 1 further hetero atom, comprising reacting the corresponding N'-aralkyl-N-cyano-amidines of the general formula (II)

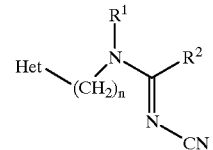

(II)

wherein

Het, n, $R^1$ and $R^2$ have the above mentioned meaning with Lawessons's reagent, optionally with a diluent and optionally with the exclusion of moisture.

6. A pesticide formulation comprising at least one N-methylenethiourea of the general formula (I) according to claim 1 and an extender and/or a surfactant.

7. A method of combating insect pests comprising applying N-methylenethioureas of the general formula (I) according to claim 1 to insect pests and/or their environment.

8. An insecticidal composition comprising at least one N-methylenethiourea of the general formula (I) according to claim 1.

9. A process for the preparation of compositions against insect pests comprising mixing N-methylenethioureas of the general formula (I) according to claim 1 with an extender and/or a surfactant.

10. A 1-thiocarbamoyl-3-N-methyl-3-N-(6-chloropyridyl-3-yl methylacetamidine of formula (I)

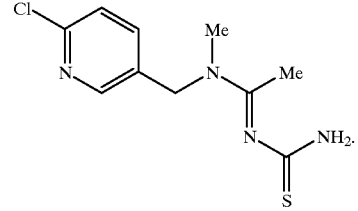

(1)

* * * * *